US008535521B2

(12) United States Patent
Lannoy (10) Patent No.: US 8,535,521 B2
(45) Date of Patent: Sep. 17, 2013

(54) OPTIMIZING CLEARANCE FOR PROTEIN-BOUND MOLECULES USING CASCADE FILTRATION THERAPY

(75) Inventor: Jean-Michel Lannoy, Anstaing (FR)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 1080 days.

(21) Appl. No.: 12/252,219

(22) Filed: Oct. 15, 2008

(65) Prior Publication Data

US 2009/0152200 A1 Jun. 18, 2009

Related U.S. Application Data

(60) Provisional application No. 60/982,396, filed on Oct. 24, 2007.

(51) Int. Cl.
  *A61M 1/34* (2006.01)
  *A61M 1/14* (2006.01)
  *B01D 61/32* (2006.01)
  *B01D 61/28* (2006.01)

(52) U.S. Cl.
  USPC .......... 210/143; 210/97; 210/134; 210/257.2; 210/258; 210/321.6; 604/4.01; 604/5.01; 604/6.09; 604/6.11

(58) Field of Classification Search
  USPC ................. 210/85, 87, 90, 97, 102, 103, 134, 210/143, 252, 257.1, 257.2, 258, 321.6; 604/4.01, 5.01, 6.09, 6.11
  See application file for complete search history.

(56) References Cited

U.S. PATENT DOCUMENTS

| 4,275,726 A | 6/1981 | Schael |
| 4,500,309 A | 2/1985 | Diedrich et al. |
| 4,661,246 A | 4/1987 | Ash |
| 4,747,950 A | 5/1988 | Guinn |
| 4,800,016 A | 1/1989 | Yang |
| 4,908,014 A | 3/1990 | Kroyer |
| 4,995,268 A | 2/1991 | Ash et al. |
| 5,000,854 A | 3/1991 | Yang |

(Continued)

FOREIGN PATENT DOCUMENTS

| WO | WO0236247 | 5/2002 |
| WO | WO02053212 | 7/2002 |

OTHER PUBLICATIONS

"Continuous Hemofiltration in the Treatment of Acute Renal Failure" by L.G. Forni, M.B., Ph.D., and P.J. Hilton, M.D., St. Thomas' Hospital, London SE1 7EH, vol. 336, No. 18, pp. 1303-1309 (1997).

(Continued)

*Primary Examiner* — John Kim
(74) *Attorney, Agent, or Firm* — K&L Gates LLP (57) ABSTRACT

A hemofiltration system or method removes unwanted molecules from a flow of blood using cascaded first and second hemofilters. Filtration of the blood in first hemofilter raises hemoconcentration of unwanted protein-bound molecules. Combination of a substitution fluid with outflow from the first hemofilter creates a concentration differential between bound and unbound molecules that frees unwanted molecules from protein bonds. Filtration of the combined fluids in a second hemofilter removes the unwanted free molecules. A second substitution fluid may be added to the twice filtered blood fluid for return to a patient. Removal of inflammatory mediators, apoptotic mediators, and certain electrolytes may be effected, and the removal may be optimized by controlling fluid flows and transmembrane pressures.

12 Claims, 5 Drawing Sheets

(56) References Cited

U.S. PATENT DOCUMENTS

| | | | |
|---|---|---|---|
| 5,011,607 A | 4/1991 | Shinzato | |
| 5,032,615 A | 7/1991 | Ward et al. | |
| 5,114,580 A | 5/1992 | Ahmad et al. | |
| 5,286,388 A | 2/1994 | Ingram | |
| 5,441,636 A | 8/1995 | Chevallet et al. | |
| 5,494,590 A | 2/1996 | Smith et al. | |
| 5,632,897 A | 5/1997 | Mathieu | |
| 5,709,993 A | 1/1998 | Buturovic-Ponikvar | |
| 5,817,046 A | 10/1998 | Glickman | |
| 5,899,874 A | 5/1999 | Jonsson | |
| 5,906,744 A | 5/1999 | Carroll et al. | |
| 5,919,163 A | 7/1999 | Glickman | |
| 6,042,784 A | 3/2000 | Wamsiedler et al. | |
| 6,139,748 A | 10/2000 | Ericson et al. | |
| 6,186,146 B1 | 2/2001 | Glickman | |
| 6,200,485 B1 | 3/2001 | Kitaevich et al. | |
| 6,217,539 B1 | 4/2001 | Goldau | |
| 6,295,990 B1 | 10/2001 | Lewis et al. | |
| 6,303,036 B1 * | 10/2001 | Collins et al. | 210/646 |
| 6,406,631 B1 * | 6/2002 | Collins et al. | 210/646 |
| 6,435,189 B1 | 8/2002 | Lewis et al. | |
| 6,471,872 B2 | 10/2002 | Kitaevich et al. | |
| 6,481,439 B1 | 11/2002 | Lewis et al. | |
| 6,548,017 B2 | 4/2003 | Krivitski et al. | |
| 6,561,997 B1 | 5/2003 | Weitzel et al. | |
| 6,566,402 B2 | 5/2003 | Warnock | |
| 6,575,927 B1 | 6/2003 | Weitzel et al. | |
| 6,585,675 B1 | 7/2003 | O'Mahoney et al. | |
| 6,610,206 B1 | 8/2003 | Callan et al. | |
| 6,716,356 B2 * | 4/2004 | Collins et al. | 210/646 |
| 6,821,441 B2 * | 11/2004 | Pedrini et al. | 210/739 |
| 6,913,588 B2 | 7/2005 | Weitzel et al. | |
| 7,074,332 B2 * | 7/2006 | Summerton et al. | 210/646 |
| 7,351,218 B2 | 4/2008 | Bene | |
| 7,517,332 B2 | 4/2009 | Tonelli et al. | |
| 7,670,491 B2 | 3/2010 | Callan et al. | |
| 7,699,806 B2 | 4/2010 | Ware et al. | |
| 2003/0031590 A1 | 2/2003 | Park | |
| 2007/0066928 A1 * | 3/2007 | Lannoy | 604/6.07 |

OTHER PUBLICATIONS

Written Opinion of the International Searching Authority for International Application No. PCT/US2008/080023.
European Office Action mailed Feb. 22, 2013, corresponding to European Patent Application No. 08841705.0.

* cited by examiner

OPTIMIZING CLEARANCE FOR PROTEIN-BOUND MOLECULES USING CASCADE FILTRATION THERAPY

RELATED APPLICATION

This application claims priority to U.S. Provisional Application No. 60/982,396 filed Oct. 24, 2007, the entire disclosure of which is incorporated by reference herewith.

FIELD

The invention relates generally to extracorporeal blood purification through hemofiltration. More specifically, the invention relates to removal, or clearance, of protein-bound molecules from blood through multiple cascaded hemofilters.

BACKGROUND

Extracorporeal blood filtration has been in widespread use for many years, most commonly in continuous renal replacement therapies (CRRT) to treat patients suffering loss or impairment of natural kidney functions. More recently, extracorporeal blood filtration has been adapted for more general application in plasmapheresis, the purification of blood through removal of noxious components circulating in the blood plasma. Considerable interest has arisen in using plasmapheresis as a means for treating ICU patients suffering from inflammatory mediator-related diseases such as septic shock, systematic inflammatory response syndrome (SIRS), and multiple organ failure (MOF). These conditions can arise from excessive release of inflammatory mediators into the bloodstream by overstimulation of the immune system. Thus, plasmapheresis as well as other CRRT have been proposed as mechanisms for removing inflammatory mediators from the bloodstream to counteract an excessive inflammatory response.

Other applications for plasmapheresis include treatment of autoimmune disorders, and treatment of severe acute pancreatitis.

In a typical hemofiltration system such as that used in plasmapheresis, blood is removed from a patient through an access site, usually by insertion of a venous catheter in a limb or central vein, and pumped through an extracorporeal circuit that includes an artificial kidney or hemofilter. The hemofilter includes a semi-permeable membrane, usually synthetic, with pore sizes selected to pass unwanted molecules. The pump provides a positive hydrostatic pressure sufficient to circulate blood along one surface of the membrane, and push water and waste products from the blood across the filter membrane and into a filtration fluid. This process, also known as ultrafiltration, causes suspended solids and solutes of high molecular weight to remain in the blood, while water and low molecular weight solutes pass through the membrane. A sterile substitution fluid, usually bicarbonate based, and having electrolyte concentrations similar to blood plasma, is added to the filtered blood to replace vital fluids and electrolytes lost through transmembrane ultrafiltration. The combined blood and substitution fluid is then returned to the patient through another venous access site.

Generally, hemofiltration is a slow continuous therapy in which sessions usually last between 12 to 24 hours. Hemofiltration processes are classified as either low-volume hemofiltration (LVH or LVHF) or high-volume hemofiltration (HVH or HVHF). The boundary between LVH and HVH is around 60 liters of ultrafiltrate per day. HVH may be administered at a rate as high as 120 liters per day.

Experimental testing suggests that certain beneficial results, e.g., higher survival rates, can be obtained from HVH, rather than LVH therapies. See, e.g., D. Journois et al., "Hemofiltration During, Cardiopulmonary Bypass in Pediatric Cardiac Surgery," Anesthesiology Vol. 81, pp. 1181-1189 (1994); A. Grootendorst et al., "I Light-Volume Hemofiltration Improves Heterodynamics of Endotoxin-Induced Shock in the Pig," Intensive Care Med., Vol. 18, pp. 235-240 (1992). It has been hypothesized that superior results of HVH may be attributable to its ability to more effectively remove noxious substances in the middle molecular weight range, such as cytokines, autacoids or apoptotic mediators.

However, several drawbacks exist to using HVH. For example, in order to support high volume blood flow, multiple catheters or a very large catheter may need to be installed in the patient to reduce resistance. Also, HVH requires larger, more expensive hemofilters with high flux membranes that can process fluid exchange in the 100 liter per day range. More critically, HVH must be carefully monitored to prevent complications. For example, the high-volume fluid exchange over a relatively short time period can cause hypothermia. To guard against hypothermia, the substitution fluid must be kept warm, and its temperature monitored over the course of treatment.

Although hemofiltration is known to be more efficient than other blood filtration therapies at the removal of middle molecular weight toxins, there is a lack of definitive evidence that hemofiltration prevents the onset of septic shock, SIRS, or MOF. Further research is required to advance the art of hemofiltration and demonstrate its efficacy in combating these potentially fatal complications.

SUMMARY

The invention provides a system or method for removing unwanted molecules from a flow of blood. Two or more hemofilters are arranged in a cascade configuration in an extracorporeal circuit, In one embodiment, a flow of blood containing unwanted molecules bound to proteins is directed through first and second cascaded hemofilters. Filtration of the blood in the first hemofilter raises the concentration of the unwanted protein-bound molecules by filtering out water and other waste solutes from the blood A substitution fluid is then combined with outflow from the first hemofilter to create a concentration differential in the combined fluid between unwanted bound molecules and unwanted free molecules. The concentration differential promotes a breakage of the protein bonds, allowing free unwanted molecules to be removed from the fluid in the second hemofilter. A second substitution fluid may be added to the twice filtered blood fluid for return to the patient. In one embodiment, the unwanted molecules may be inflammatory mediators, apoptotic mediators, or electrolytes.

In one embodiment, a system may be equipped with one or more pumps, sensors, and related instrumentation and controls to effect blood purification using LVH or HVH. Sensor feedback to a central controller may be used to maintain proper flow, pressure, and temperature characteristics in the extracorporeal circuit, such as flow rate of blood through a hemofilter, or transmembrane pressure across a hemofilter semipermeable membrane. These characteristics may be automatically adjusted by controller algorithms to optimize the clearance or removal rate of the unwanted molecules.

Some methods may include process steps of raising concentration in the blood flow of unwanted molecules bound to proteins, creating in the blood flow a concentration differential between the unwanted molecules bound to proteins and unwanted molecules free of protein bonds, and filtering the blood flow in a hemofilter to remove the free unwanted molecules. Some methods may include directing a flow of the blood through a first hemofilter, combining a substitution fluid with outflow from the first hemofilter to free unwanted molecules from protein bonds, and directing the combined outflow and substitution fluid through a second hemofilter to filter out the free unwanted molecules.

BRIEF DESCRIPTION OF THE DRAWINGS

The features, objects, and advantages of the invention will become more apparent from the detailed description set forth below when taken in conjunction with the drawings, wherein.

DETAILED DESCRIPTION

The invention provides a system or method for removing unwanted molecules from blood. The invention may be applied as a stand-alone system for purifying blood, or with an extacorporeal blood filtration circuit used for plasmapheresis. Another application may be a hemofiltration system used as an artificial kidney or for blood purification during CRRT. Other applications may include therapies intended to remove unwanted molecules from blood such as inflammatory mediators, apoptotic mediators, various electrolytes, and other substances capable of being cleared from the blood through semi-permeable membranes.

A system or method may be applied as a hemofiltration therapy, either as HVH or LVH. To tally appreciate the nature of the problem being solved by the invention, a summary of research into HVH therapies conducted by the inventor is provided. An investigation by the inventor into why HVH therapy may be effective in removing inflammatory mediators, and why MOF passes from one organ to another, revealed that a principle transporting mechanism for inflammatory mediators is protein. Specifically, the protein albumin was determined to be one such mechanism.

In HVH therapy, the procedural principle is removal of plasma fluid from blood through a hemofilter, and replacement of the lost fluid by addition of substitution solution. An analysis of hemofiltration therapies revealed that HVH removes different quantities of certain molecules than LVH therapies. For example, Ronco showed that HVH can be effective at removing inflammatory mediators, whereas LVH has no effect on plasma levels of inflammatory mediators. C. Ronco, "Pulse High-Volume Haemofiltration in Sepsis," European Renal and Genito-Urinary Disease, pp. 39-45, 2006. Experiments conducted by the inventor compared results of LVH versus HVH therapies. An analysis of solution filtered using LVH showed no significant presence of free mediators within the filtered fluid. Free mediators were identified, however, in the solution filtered using HVH. This leads to a hypothesis that the different results of LVH versus HVH may be attributable to a majority of inflammatory or apoptotic mediators being fixed and transported by protein such as albumin.

When HVH is used or when LVH is used, the filtrate ratio between blood volume treated per minute and plasma volume treated per minute is essentially the same. Both techniques create an increase of protein concentration inside the hemofilter because the bonded proteins remain in the blood. In other words, the hemoconcentration increases as water and other waste products are filtered from the blood flow through the filter membrane and into a filtration fluid. Downstream of the hemofilter, a substitution fluid is added to the blood flow to replace fluid volume lost through the hemofilter. During this addition, with respect to a particular protein-bound mediator, a concentration difference is created between the blood and the substitution fluid. The difference occurs because the blood contains a high concentration of a protein-bound mediator, while the substitution fluid is essentially mediator free. This condition promotes a break of liaison, or breakage of the bond, between mediators and protein, resulting in a higher concentration of free mediators once the two fluids (blood and substitution) have combined.

The liberation of mediators that occurs after addition of a substitution fluid explains why HVH may be more effective than LVH at mediator removal. LVH moves blood at a slower rate than HVH. Therefore, free mediators in an LVH blood flow move more slowly, and have more time to become back-bound to protein as the blood returns to the patient to run its course. By the time the blood cycles back to the extracorporeal circuit, little or no free mediators remain. On the other hand, with HVH, blood flow that is faster allows a higher percentage of free mediators to remain unbound after cycling back through the patient. Thus, in a subsequent trip through the hemofilter, the free mediators, having a smaller molecular weight than protein bound mediators, are more likely to be filtered out of the blood flow through the filter membrane before they can bound back to protein.

Figure 1:
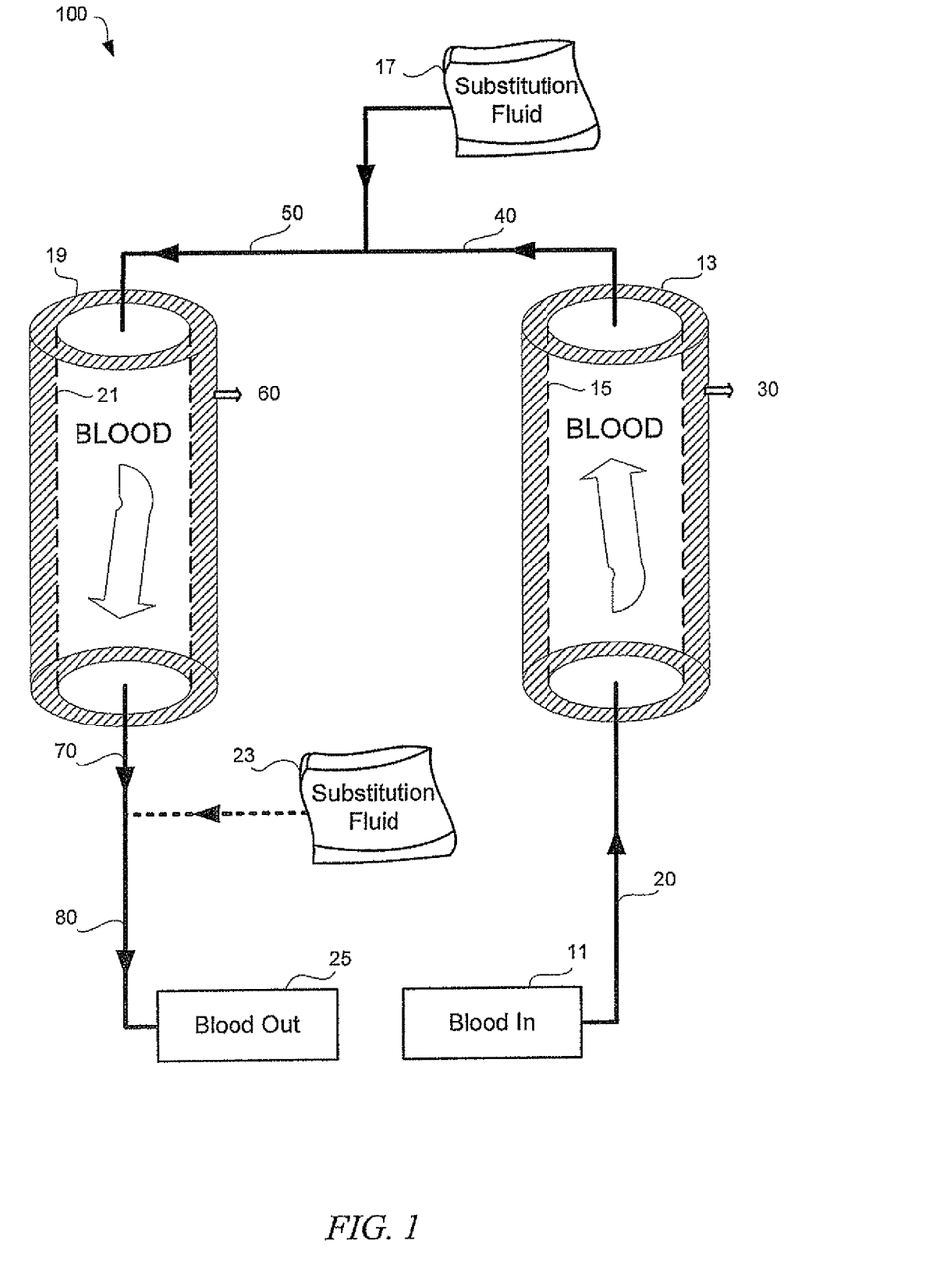
FIG. 1 is a schematic diagram of a blood filtration system for removing unwanted molecules from blood according to an embodiment.

Systems and methods exploit the temporal free mediator condition by effecting hemofiltration in multiple stages. An embodiment of the invention is shown in FIG. 1. The embodiment shows a flow of blood in a counterclockwise direction beginning with a source 11 of unfiltered blood. Source 11 provides a blood flow, 20, containing unwanted molecules that enter a first hemofilter 13. In one embodiment, the unwanted molecules may include mediators bound to protein. Through osmotic or hydrostatic pressure, the first hemofilter 13 may remove water and waste solutes from the blood flow 20. The first hemofilter 13 may contain a semi-permeable membrane 15 that passes molecules and solute below a selected molecular weight or smaller than a selected pore size. The water and waste solutes may exit the first hemofilter 13 as a filtrate 30. Thus, the filtered blood flow 40 exiting the first hemofilter 13 may have a higher hemoconcentration, and may therefore have a higher concentration of protein bound mediators.

To replenish volume lost through the first hemofilter 13, a substitution fluid 17 may be added to the blood flow 40, forming a combined flow 50. The substitution fluid 17 may contain little or no free molecules or mediators of the unwanted type. Therefore, in the combined flow 50, a concentration difference may occur with respect to the unwanted molecules between the concentration in the blood flow 40 and the concentration in the substitution fluid 17. This difference may promote a break of liaison, or breakage of the molecular bond, between unwanted molecules and protein.

The combined flow 50 may enter a second hemofilter 19. The second hemofilter 19 provides a second stage of filtration for the blood, and may be referred to as being in a series or cascade relation to the first hemofilter 13. At this stage, the combined flow 50 may ideally have a higher concentration of unbounded unwanted molecules than the blood flow 20 or the blood flow 40. The second hemofilter 19 may contain a semi-permeable membrane 21 that passes molecules and solute below a selected molecular weight or smaller than a selected pore size, and may be rated differently than the first hemofilter 13. Thus, water and waste solutes, including unwanted molecules or unwanted free mediators, may exit the second hemofilter 19 as a waste filtrate 60, thereby removing them from the blood.

The twice filtered blood flow 70 exits the second hemofilter 19. An optional second substitution fluid 23 (indicated as optional by a dashed flow line) may be provided to replenish fluid volume lost through the second hemofilter 19. When the second substitution fluid 23 is present in the circuit, a combined flow 80 is produced that includes blood flow 70 and the second substitution fluid 23. Combined flow 80 may be necessary, for example, for returning sufficient volume of twice filtered blood directly to a patient. Otherwise, the twice filtered output may exit system 100 at a blood collection point 25.

Although only two cascaded hemofilters are shown in the foregoing example, it is certainly possible within the scope of the invention to employ any number of additional cascaded filtration stages. By cascading two or more hemofilters in the extracorporeal circuit, free mediators liberated during an injection of substitution fluid downstream of a hemofilter may be filtered from the blood in a subsequent hemofilter before the blood fluid is collected or returned to a patient. Thus, cascade filtration may be just as effective as using LVH as it would be using HVH. By using LVH with cascade filtration, the disadvantages of HVH, e.g., larger access sites, larger or multiple catheters, larger hemofilters, and risk of hypothermia, can be avoided.

Figure 2:
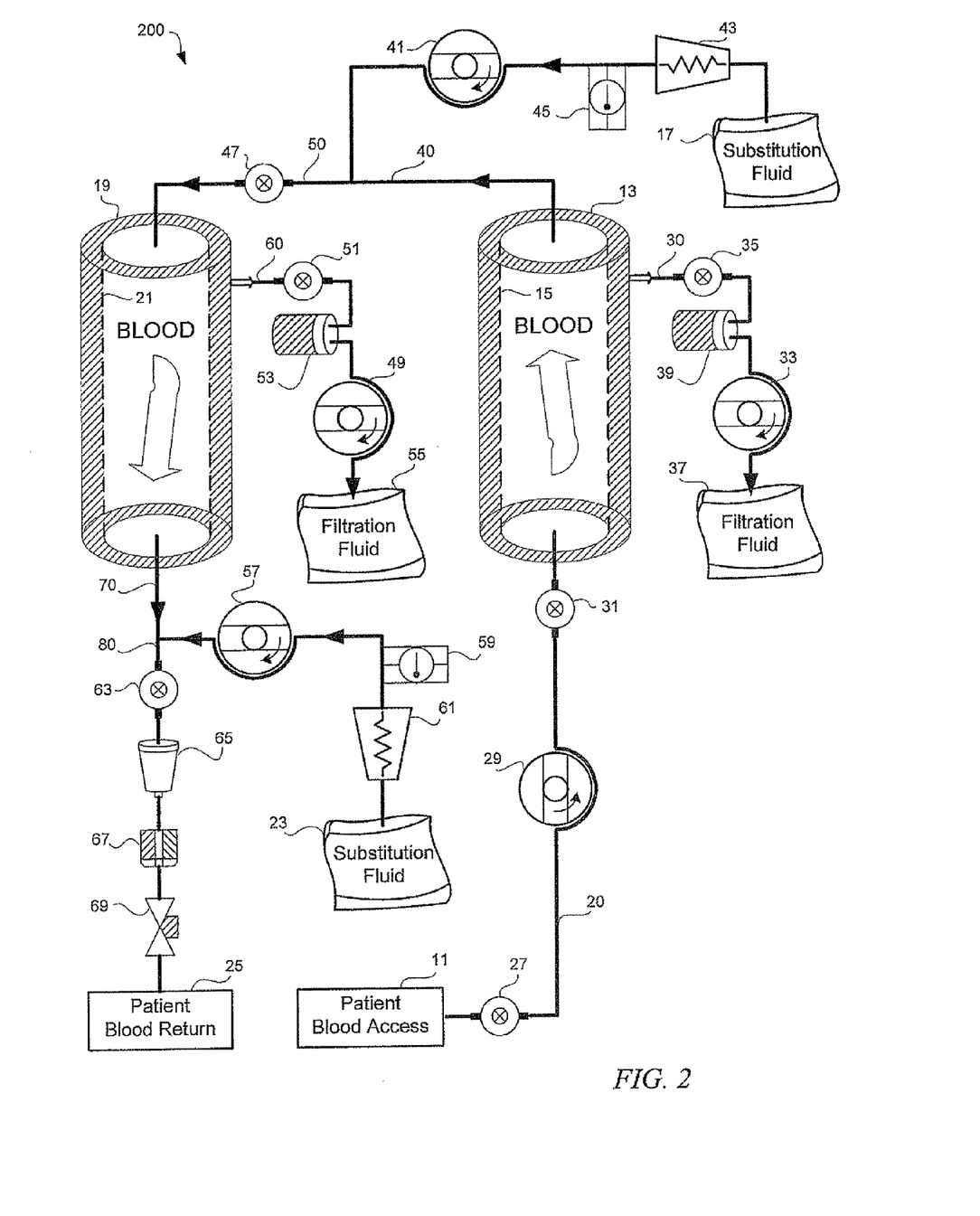
FIG. 2 is a schematic diagram of an extracorporeal blood filtration system for removing unwanted molecules from blood according to an embodiment.

Another exemplary embodiment of a system according to the invention is shown in FIG. 2. System 200 may be used in combination with other CRRT equipment, such as a dialysis machine or other advanced CRRT Systems such as that described in copending application U.S. patent application Ser. No. 11/525,800 entitled "Automation and Optimization of CRRT Treatment Using Regional Citrate Anticoagulation" (incorporated by reference herein), or in other extracorporeal CRRT or plasmapheresis systems, or in hemofiltration systems employing LVH or HVH therapies and the like. As such, some or all of the components of system 200 may form an integral part of the extracorporeal circuit.

The components and operation of the extracorporeal circuit of system 200 are now described following blood flow in a counterclockwise direction beginning at patient access site 11 at the bottom of the figure. Patient access site 11 may represent one or more intravenous (I-V) catheters, PICC lines or central venous catheters or equivalent means for penetrating a blood vessel of the patient to draw a flow of unfiltered blood into the extracorporeal circuit. A sensor 27, which may be a blood flow detector or blood pressure sensor, may be provided to measure the flow or pressure of blood leaving the patient at the patient access site 11. The sensor 27 may be any commercial detector known in the art and commonly used for this purpose, such as a non-invasive infrared or ultrasonic Doppler type detector. In one embodiment, the sensor 27 may be a pressure sensor for detecting a differential pressure between two points in the blood flow, for derivation of a signal representative of the blood flow. In this and other embodiments, additional sensors may be located at various points in the circuit. Hereinafter, the sensors will be disclosed as pressure sensors, although it should be appreciated that flow sensors may also be employed.

A blood pump 29 provides the mechanical force to sustain a continuous flow of blood 20. The blood pump 29 may be any conventional pump known in the medical arts and suitable for the purpose. It should be understood that the blood pump 29, as well as other pumps described herein or otherwise used in different embodiments of the invention, may be conventional diaphragm, centrifugal, or peristaltic pumps typically used in the medical arts.

A pre-filter sensor 31 may be installed to measure pressure in blood flow 20 upstream of a first hemofilter 13. The first hemofilter 13 may be of conventional design and selected from commercial stock, and may include two flow paths separated from each other by a semi-permeable membrane 15. The semi-permeable membrane 15 may be selected for its particular pore size, i.e. its ability to pass molecules up to a certain atomic weight.

By osmotic or hydrostatic pressure, water and waste solutes in blood flow 20 pass through the semi-permeable membrane 15 and exit the first hemofilter 13 along one flow path as a filtrate flow 30. A filtrate pump 33 may be installed to draw filtrate flow 30 from the first hemofilter 13. A sensor 35 may be located in filtrate flow 30 to measure pressure in that line. Filtrate in flow 30 may be collected in a filtrate collector 37, and may ultimately be disposed of as a waste product.

A blood leak detector 39 may also be installed in the filtrate flow path to detect excessive presence of blood plasma. One example of a blood leak detector 39 is a non-invasive optical sensor manufactured by Introtek Intl. of Edgewood, N.Y. The Introtek leak detector operates on the principle of light absorption. Filtrate flow may be routed to the leak detector through clear plastic tubing, into which a beam of light is directed. The specific amount of light absorbed by the filtrate is compared to a calibrated pre-set threshold. If the threshold is exceeded due to the presence of too much blood leaking into flow path 30 through a perforation in the semi-permeable membrane 15, the optical leak detector may output an analog or digital alarm signal to indicate an out-of-tolerance condition.

The second flow path in the first hemofilter 13 is provided for filtered blood, which exits the first hemofilter 13 as blood flow 40 on the downstream side. A first substitution fluid 17 may be provided to add volume to blood flow 40 to compensate for volume lost as filtrate flow 30. The first substitution fluid 17 may be any sterile intravenous fluid having a desired concentration of electrolytes, such as a dialysate solution commonly known in the art. Additionally, the first substitution fluid 17 may be formulated as a buffer to maintain a desired acid-base balance. For example, the first substitution fluid 17 may be an acetate-based, lactate-based, citrate-based or bicarbonate-based buffer. In other embodiments, the first substitution fluid 17 may include one or more anticoagulants such as heparin or citrates.

A substitution fluid pump 41 may be installed to force the first substitution fluid 17 to combine with blood flow 40. A heater 43 may be installed in the flow path of the first substitution fluid 17 to maintain proper temperature levels and prevent hypothermia, particularly for HVH operations. A temperature sensor 45 may also be installed to sense and transmit an analog or digital signal representing substitution fluid temperature to a controller (not shown) to effect temperature control, which will be discussed below in greater detail.

The first substitution fluid 17 combines with blood flow 40 to form a supplemented flow 50 upstream of a second hemofilter 19. In one embodiment, an intermediate pressure sensor 47 may be placed into the path of the supplemented flow 50 for making pressure or flow measurements at that point, and may transmit a signal representing pressure or flow to a controller. The supplemented flow 50 creates a concentration differential that liberates bound unwanted molecules (or bound inflammatory or apoptotic mediators) from protein bonds according to the hypothesis previously described. The combined flow containing free, unwanted molecules may then enter the second hemofilter 19.

The second hemofilter 19 may function similarly to, and be of the same general construction as the first hemofilter 13. The second hemofilter 19, however, may include a semi-permeable membrane 21 that differs in construction from the semi-permeable membrane 15. In particular, the semi-permeable membrane 21 may be selected for a pore size designed to pass a particular unwanted molecule or mediator. A first flow path exiting the second hemofilter 19 may be provided as a filtrate flow 60 for passing water and unwanted wastes out of the blood through osmotic or hydrostatic pressure. A filtrate pump 49 may be installed to draw the filtrate flow 60. As in flow path 30, the discharge line for filtrate flow 60 may also be equipped with a flow or pressure sensor 51, a blood leak detector 53, and a filtrate collector 55.

In one embodiment, the second hemofilter 19 may be selected for a membrane pore size that passes unwanted inflammatory mediators. In another embodiment, the second hemofilter 19 may be selected for a membrane pore size that filters out apoptotic mediators. In another embodiment, the second hemofilter 19 may be selected for a membrane pore size that removes calcium ions. In a second flow path exiting the second hemofilter 19, a twice filtered flow of blood 70 exits the second hemofilter 19 free or relatively free of unwanted molecules, mediators, or electrolytes.

A second substitution fluid 23 may be added to blood flow 70 downstream of the second hemofilter 19. A substitution fluid 23 may be pumped into blood flow 70 using a substitution fluid pump 57. The addition of the substitution fluid 23 to twice filtered blood flow 70 compensates for fluid lost through the second hemofilter 19 as filtrate flow 60. Like the substitution fluid 17, the substitution fluid 23 may be any sterile, intravenous fluid formulated as desired. In one embodiment, a temperature sensor 59 and a heater 61 may be installed as shown for controlling temperature of the substitution fluid 23.

Combining the substitution fluid 23 with twice filtered blood flow 80 creates a combined blood flow 80 at a point downstream of the second hemofilter 19. In one embodiment, a pressure sensor 63 may be located in the circuit at this point for pressure or flow measurements. In other embodiments, an air bubble trap 65, an air bubble detector 67, and/or an automatic clamp 69 may be installed in the circuit as safety precautions at points upstream of a patient blood return site 25. The air bubble trap 65 may be placed into blood flow 80 for removal of unwanted micro bubbles. The air bubble detector 67 may be placed into blood flow 80 downstream of the air bubble trap 65, and preferably downstream of all pumps in the circuit, to detect the undesirable presence of air bubbles or air gaps in blood flow 80. Any air bubble detector known in the medical arts, such as ones operating on ultrasonic or infrared sensing technology, may be used for this purpose. The automatic clamp 69 may be placed between the air bubble detector 67 and a patient blood return site 25. In one embodiment, a solenoid valve may be employed as the automatic clamp 69. In another embodiment, the air bubble detector 67 and the automatic clamp 69 interface electronically with a controller. The return site 25 may be provided using an appropriate or complimentary catheterization method as used for access site 11.

Figure 3:
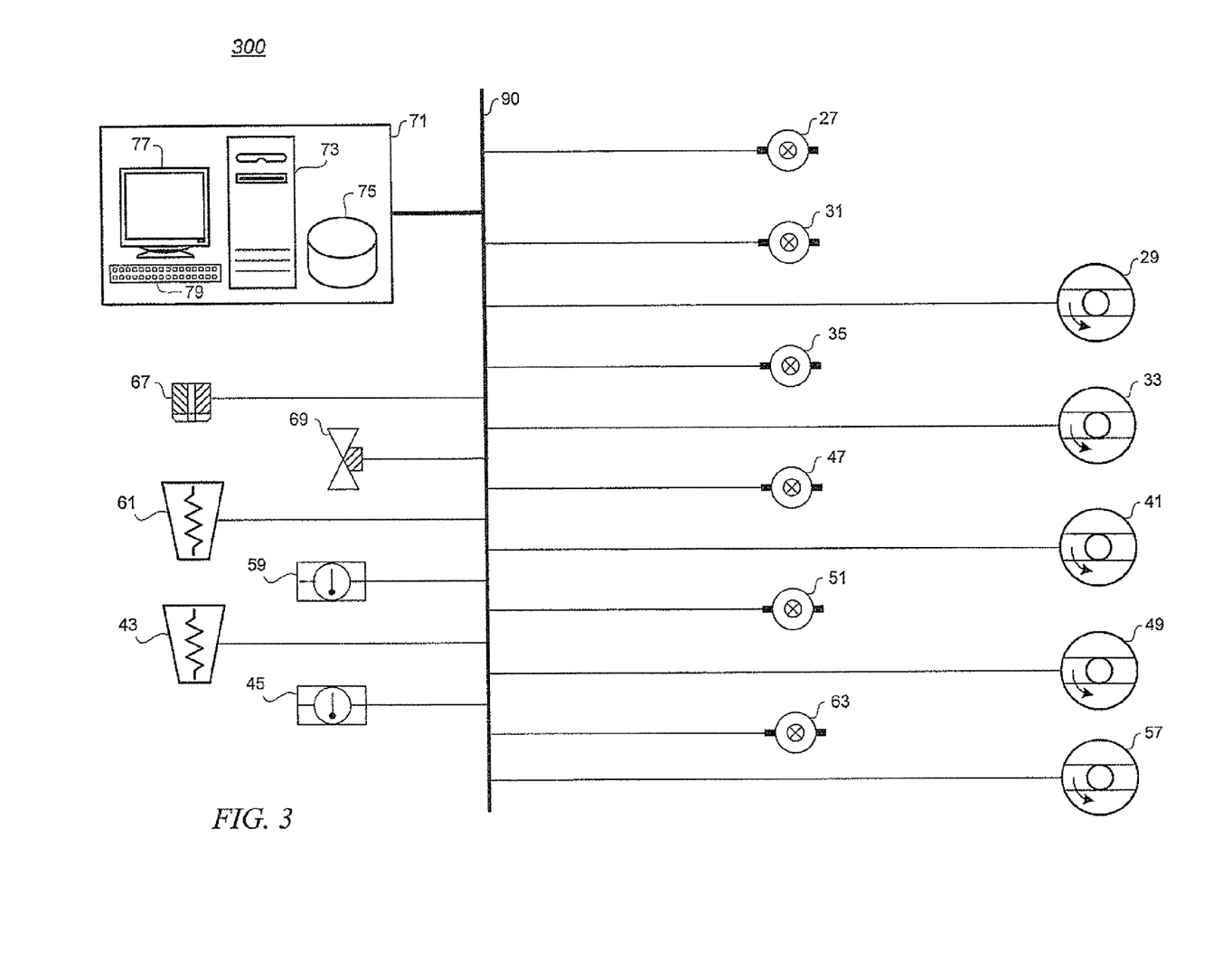
FIG. 3 is a schematic diagram of a system for controlling the rate of removal of unwanted molecules according to an embodiment.

FIG. 3 illustrates a schematic diagram of one embodiment of a system 300 according to the invention for controlling a removal rate of unwanted molecules in a hemofiltration circuit such as that of system 200. A central computer or controller 71 may allow a user to manually or automatically control components within the hemofiltration circuit. The components may include the blood pump 29, the first filtrate pump 33, the first substitution fluid pump 41, the second filtrate pump 49, the second substitution fluid pump 57, the first substitution fluid heater 43, the second substitution fluid heater 61, and the automatic clamp 69. Control loops may be enabled by the controller 71 communicating with and/or receiving sensory input from various instrumentation within the hemofiltration circuit. The instrumentation may include the patient access pressure sensor 27, the pre-filter pressure sensor 31, the first filtrate pressure sensor 35, the intermediate pressure sensor 47, the second filtrate pressure sensor 51, the patient return pressure sensor 63, the first substitution fluid temperature sensor 45, the second substitution fluid temperature sensor 59, and the air bubble detector 67. The controller 71 may communicate with each of the instruments, and may issue automatic control signals to each of the components, via a bus or signal line 90. The signal line 90 may be made up of one or more electrical cables or groups of electrical cables or buses suitable for analog or digital signal transmission. In another embodiment, the bus 90 may also represent one or more wireless links.

The controller 71 may include a CPU 73, which may be a general purpose computer, personal computer, or other suitable microprocessor-based component or microcontroller known in the art. A computer-readable memory 75, accessible by CPU 73, may be integral to CPU 73 or may be separately coupled thereto. The memory 75 may include hardware and/or software, executable by CPU 73, for effecting various controller functions including receiving system input signals and transmitting output control signals. The memory 75 may also include any conventional operating system software essential for basic computing operations. The controller 71 may further include peripheral devices such as a display unit 77 and a user interface 79. The display unit 77 and the user interface 79 may assist a user during manual operation of the system. For example, the controller 71 may perform a calculation for determining a flow rate within the extracorporeal circuit, such as a flow rate for flow 20, flow 30, flow 40, flow 50, flow 60, flow 70 or flow 80. The controller 71 may also cause the results of the calculation to display on display unit 77. A user reading these results may then adjust a circuit component manually. Or, the user may adjust the component remotely by manual entry of keystrokes on the user interface 79.

System 300 may operate by the controller 71 automatically controlling flow rates and temperatures within the extracorporeal circuit in response to settings specified or input through the user interface 79. The controller 71 may then maintain specified flow rates using feedback received from instrumentation such as the pressure or flow sensors. In one embodiment, the CPU 73 may calculate a control signal for a pump by executing an algorithm stored in the memory 75. The controller 71 may then transmit an output signal representing pump speed to one or more of the pumps, which, in response to receiving the output signal, adjusts its speed to achieve a specified flow rate. In one embodiment, the output signal to a pump may be a voltage level. In another embodiment, the controller 71 may control fluid temperature to maintain it within specified limits. For example, the temperature sensor 45 may transmit a signal representing the sensed temperature of the first substitution fluid 17 to the controller 71 over the bus 90. In response, the CPU 73 may execute a control algorithm stored in the memory 75 to calculate an output signal for transmission over the bus 90 to the heater 43. The output signal to the heater 43 may be a control signal that varies the amount of electrical current energizing an electric heating element of the heater 43, or it may turn the heating element on and off. In this way, the temperature of fluid flow within the circuit may be maintained at an optimal level when delivered back to the patient. Feedback control algorithms for controlling pump speeds and temperatures, such as PID or state-space control algorithms, are well known in the art.

Using another control loop, the controller 71 may be configured to shut down the hemofiltration circuit in response to receiving an alarm signal over the bus 90 from the air bubble detector 67. In this case, the controller 71 may output an actuation signal over the bus 90 to effect closure of the automatic clamp 69. In one embodiment, the actuation signal may be a voltage of sufficient potential to energize a solenoid to produce a magnetic force sufficient to close a valve in the automatic clamp 69, thereby stopping flow to the patient return site 25. In another embodiment, the actuation signal may also shut down one or more pumps in the circuit.

In another embodiment, the CPU 73 may calculate and control differential pressures at various points of interest in the extracorporeal circuit. If results of any of these calculations indicate an out-of-tolerance condition, the controller 71 may adjust flow rates of one or more pumps, shut down the circuit, or issue audible or visual alarms. For example, transmembrane pressure (TMP) across a hemofilter may be specified by a user, or rated by a hemofilter manufacturer, within a certain tolerance range. The controller 71 may determine TMP_1 for the first hemofilter by reading inputs from pressure sensors within the circuit, and performing a calculation. In this example, TMP_1 may be calculated as:

$$TMP\_1 = (PRE\_1 + INT)/2 - FILT\_1$$

where PRE_1 is the pre-filter pressure at sensor 31, INT is the intermediate pressure at sensor 47, and FILT_1 is the first filtrate pressure at the sensor 35. In one scenario, if a calculated value for TMP_1 exceeds a specified range, this may indicate excess clotting of blood in the semi-permeable membrane of the first hemofilter 13. The controller 71 may then issue an audible alarm, or a visual alarm such as illuminating a warning light or displaying a warning or instruction on the display unit 77.

Similarly, a transmembrane pressure TMP_2 in the second hemofilter 19 may be calculated as:

$$TMP\_2 = (INT + RET)/2 - FILT\_2$$

where RET is pressure at the patient return site at the sensor 63, and FILT_2 is the second filtrate pressure at the sensor 51.

The controller 71 may also calculate and control pressure drop, PD, through any of the hemofilters according to a user-specified input. For example, PD_1 through the first hemofilter 13 and PD_2 through the second hemofilter 19 may be calculated as:

$$PD\_1 = PRE\_1 - INT + \text{offset}\_1$$

$$PD\_2 = INT - RET + \text{offset}\_2$$

where offset_1 and offset_2 are correction values for PD_1 and PD_2, respectively, to account for positioning offset errors between the pressure sensors used for the particular calculation.

The specified PD across a hemofilter, the flow through a hemofilter, the pore size of a semi-permeable membrane, and a TMP across a hemofilter may all affect the ultrafiltration rate of a hemofilter, and thus the rate at which unwanted molecules or mediators may be removed from the blood. Thus, the removal rate of unwanted molecules could controlled by adjusting one or more of PD, TMP, pore size, or blood flow at any point in the circuit. By selecting these parameters carefully, a hemofiltration circuit according to the invention, through manual adjustments and/or automatic control, may optimize clearance of protein bound molecules through cascade filtration therapy.

It should be appreciated that the controller 71 is not limited to controlling only those components and instruments shown in the systems 200 and 300. The invention may be integrated with many other CRRT, dialysis, or plasmapheresis systems. In particular, the invention may be integrated with systems and methods described in co-pending U.S. patent application Ser. No. 11/525,800 entitled "Automation and Optimization of CRRT Treatment Using Regional Citrate Anticoagulation," filed Sep. 21, 2006. Accordingly, the controller 71 may include means for optimizing citrate anticoagulation during administration of the hemofiltration therapy.

Figure 4:
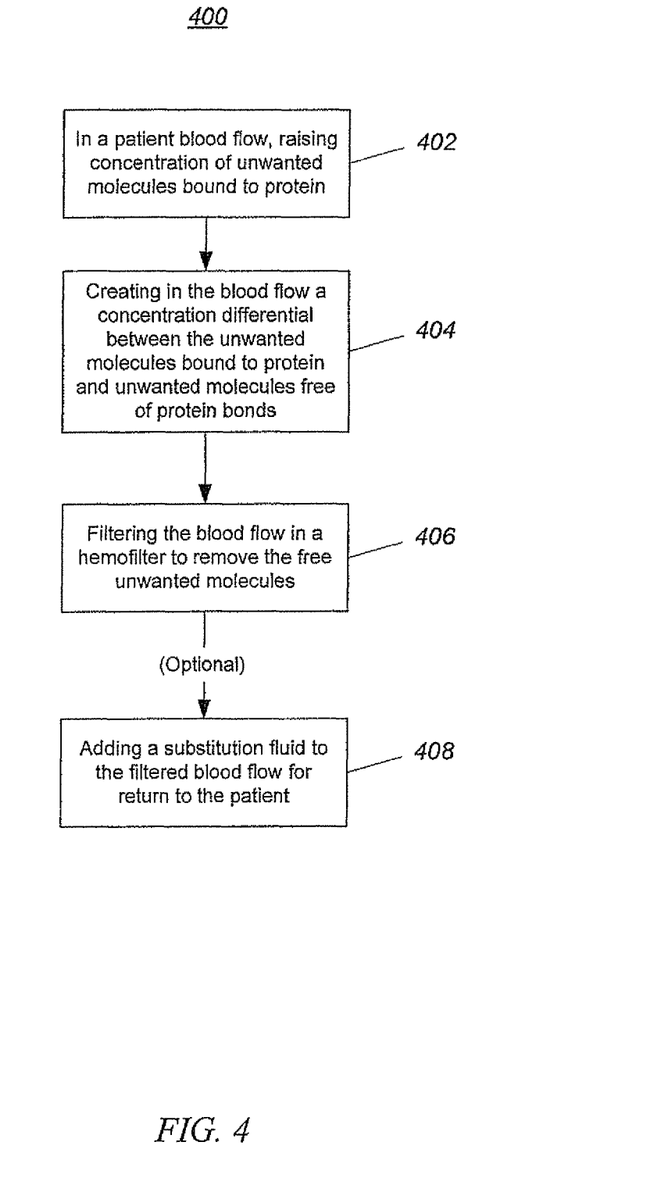
FIG. 4 is a flow chart of a method for removing unwanted molecules from blood according to an embodiment.

FIG. 4 is a flow chart of a method 400 for removing unwanted molecules from blood according to an embodiment. Method 400 may be performed within the context of operating one or more systems of the invention described in the foregoing embodiments. Method 400 is a process for optimizing removal of unwanted molecules from a flow of blood. At step 402, the method may raise concentration, in the blood flow, of unwanted molecules bound to proteins. One example of executing this step is given in the foregoing discussion of system 100, wherein a molecular concentration may be raised by filtering water and waste products from blood using a hemofilter. Other ways of executing this step may also be carried out within the scope of the invention, such as by centrifuge. In step 404, the method may create in the blood flow a concentration differential between the unwanted molecules bound to proteins and unwanted molecules free of protein bonds. An example of executing this step, described above, may be adding a sterile substitution fluid to the concentrated blood. Other fluids, such as blood plasma free of the unwanted molecules, may also be used to create the concentration differential. In step 406, the method may filter the blood flow in a hemofilter to remove free unwanted molecules. In a case where the method is used for purifying blood from a patient, e.g. during a CRRT, optional step 408 may also be executed. In step 408, the method may add a substitution fluid to the filtered blood flow to establish proper blood chemistry, such as proper electrolyte and pH levels, before returning the blood to the patient.

Figure 5:
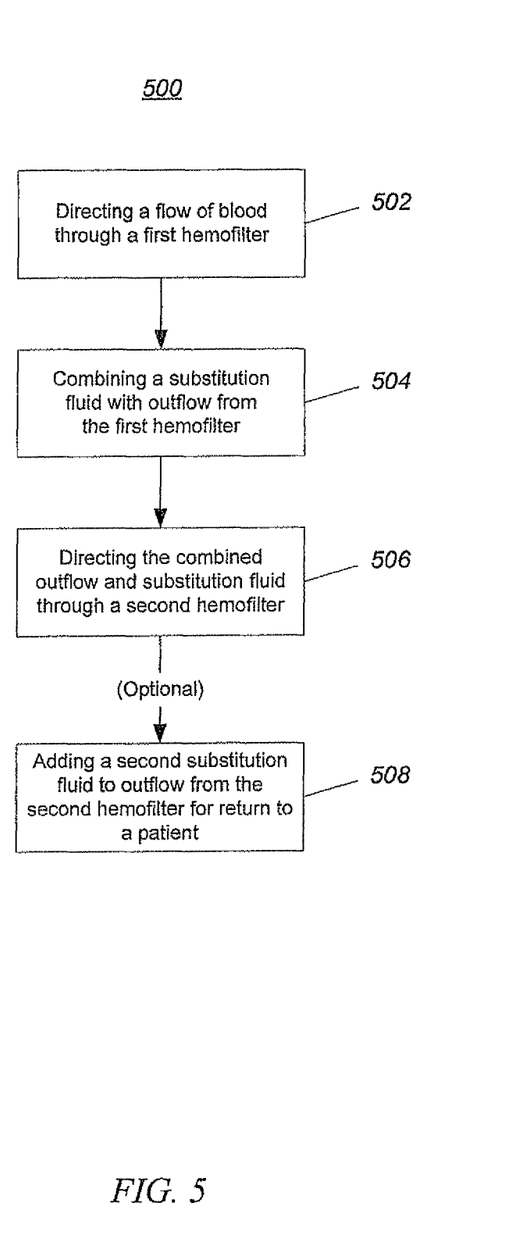
FIG. 5 is a flow chart of another method for removing unwanted molecules from blood according to an embodiment.

FIG. 5 is a flow chart of another method 500 for removing unwanted molecules from blood according to an embodiment. Method 500 depicts another set of process steps for optimizing removal of unwanted molecules from a flow of blood, and may also be performed within the context of operating one or more systems of the invention previously described. In step 502, a flow of blood may be directed through a first hemofilter. Step 502 may remove water and waste products from the blood flow, and may also raise concentration of an unwanted molecule or mediator in a protein-bonded state. In step 504, outflow from the first hemofilter may be combined with a substitution fluid. Step 504 may promote a breakage of the protein bonds, creating a higher concentration of free unwanted molecules or free unwanted mediators. In step 506, the combined flow of concentrated blood and substitution fluid may be directed through a second hemofilter, Step 506 may remove unwanted molecules or unwanted mediators from the blood. In an optional step 508, a second substitution fluid may be added to outflow from the second hemofilter prior to returning the fluid to a patient.

The invention has been disclosed in an illustrative style. Accordingly, the terminology employed throughout should be read in an exemplary rather than a limiting manner. Although minor modifications of the present invention will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. An extracorporeal blood filtration system for removing unwanted molecules from a flow of blood from a patient, comprising:
    a first hemofilter raising hemoconcentration of the blood in a filtered blood flow by removing a volume of fluid from the blood;
    a first substitution fluid;
    a controller controlling flow of the first substitution fluid so that the first substitution fluid supplements the filtered blood flow in an amount substantially equal to the volume of fluid removed from the blood in the first hemofilter;
    a second hemofilter filtering unwanted molecules from the supplemented blood flow; and
    a second substitution fluid supplementing outflow from the second hemofilter for return to the patient.

2. The system of claim 1 wherein the first substitution fluid supplementing the filtered blood flow frees the unwanted molecules from protein bonds.

3. The system of claim 2 wherein the second hemofilter includes a membrane having pore sizes selected to pass the free unwanted molecules.

4. The system of claim 1 further comprising a means for adjusting blood flow through the first hemofilter.

5. The system of claim 1 further comprising a means for adjusting transmembrane pressure in the first hemofilter.

6. The system of claim 1 further comprising a means for adjusting supplemented blood flow through the second hemofilter.

7. The system of claim 1 further comprising a means for adjusting transmembrane pressure in the second hemofilter.

8. The system of claim 1 wherein the unwanted molecules include one or more mediators.

9. The system of claim 1 wherein the controller optimizes the removal rate of the unwanted molecules from the blood flow.

10. The system of claim 9 wherein the controller adjusts one or more of blood flow in the first hemofilter, blood flow in the second hemofilter, transmembrane pressure in the first hemofilter, transmembrane pressure in the second hemofilter, flow of the first substitution fluid, flow of the second substitution fluid, pressure drop across the first hemofilter, and pressure drop across the second hemofilter.

11. The system of claim 1, wherein the first and second hemofilters differ in construction to filter molecules of different pore sizes.

12. The system of claim 1, wherein at least one of the first and second substitution fluids is heated by a heater.

* * * * *

UNITED STATES PATENT AND TRADEMARK OFFICE
CERTIFICATE OF CORRECTION

| | | |
|---|---|---|
| PATENT NO. | : 8,535,521 B2 | Page 1 of 1 |
| APPLICATION NO. | : 12/252219 | |
| DATED | : September 17, 2013 | |
| INVENTOR(S) | : Lannoy | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1093 days.

Signed and Sealed this
Seventh Day of April, 2015

Michelle K. Lee
*Director of the United States Patent and Trademark Office*